(12) United States Patent
Boyarsky et al.

(10) Patent No.: US 8,110,819 B2
(45) Date of Patent: Feb. 7, 2012

(54) COMPUTER PERIPHERALS STERILIZATION SYSTEM

(76) Inventors: Oleg D. Boyarsky, Cherry Hill, NJ (US); David Boyarsky, Cherry Hill, NJ (US)

( * ) Notice: Subject to any disclaimer, the term of this patent is extended or adjusted under 35 U.S.C. 154(b) by 179 days.

(21) Appl. No.: 12/624,824

(22) Filed: Nov. 24, 2009

(65) Prior Publication Data

US 2010/0127189 A1 May 27, 2010

Related U.S. Application Data

(60) Provisional application No. 61/117,287, filed on Nov. 24, 2008.

(51) Int. Cl.
*A61L 2/10* (2006.01)

(52) U.S. Cl. ........... 250/492.1; 250/454.11; 250/455.11; 422/24

(58) Field of Classification Search .................. None
See application file for complete search history.

(56) References Cited

U.S. PATENT DOCUMENTS

| | | | |
|---|---|---|---|
| 2,822,476 A | 2/1958 | Osgood | |
| 3,454,075 A | 7/1969 | Weinstein | |
| 4,922,980 A | 5/1990 | Parker | |
| 5,920,075 A | 7/1999 | Whitehead | |
| 5,944,432 A | 8/1999 | Richardson | |
| 6,278,122 B1 | 8/2001 | Gagnon | |
| 6,458,331 B1 | 10/2002 | Roberts | |
| 6,720,950 B2 | 4/2004 | Cheng | |
| 6,953,940 B2 | 10/2005 | Leighley et al. | |
| 7,227,534 B2 | 6/2007 | Lin et al. | |
| 7,372,044 B2 | 5/2008 | Ross | |
| 7,692,159 B2 * | 4/2010 | Lane et al. | 250/455.11 |
| 2004/0028553 A1 | 2/2004 | Panico | |
| 2006/0147339 A1 | 7/2006 | Hunter et al. | |
| 2008/0067417 A1 | 3/2008 | Lane et al. | |
| 2008/0253941 A1 * | 10/2008 | Wichers et al. | 422/186.3 |
| 2008/0260601 A1 | 10/2008 | Lyon | |
| 2009/0123331 A1 | 5/2009 | Ross | |
| 2009/0218512 A1 | 9/2009 | Ranta et al. | |

FOREIGN PATENT DOCUMENTS

KR     1020070057715 A  *  7/2007

* cited by examiner

*Primary Examiner* — Jack Berman
(74) *Attorney, Agent, or Firm* — John F. Letchford; Archer & Greiner, P.C.

(57) ABSTRACT

A system and method including a wand-type ultraviolet (UV) light assembly positioned above a keyboard and other computer peripheral device(s) to be sanitized. The UV light assembly is preferably moved across the peripheral device surface to eliminate nearly all germs, bacteria, viruses, pathogens and other microorganisms that have accumulated on the surfaces of the keyboard and other peripherals. Desirably, the system operation is managed by a controller device which is in communication with a host computer. In addition, the system allows for the collection and analysis of system performance data. The invention provides an extremely effective, compact, virtually cost-free and environmentally-friendly solution to disinfecting surfaces of keyboards and other peripheral devices.

13 Claims, 2 Drawing Sheets

COMPUTER PERIPHERALS STERILIZATION SYSTEM

CROSS REFERENCE TO RELATED APPLICATION

The present application claims the benefit of U.S. Provisional Patent Application No. 61/117,287, filed Nov. 24, 2008, which is incorporated herein by reference in its entirety.

FIELD OF THE INVENTION

The present invention relates in general to systems and methods for protecting computer peripheral equipment and other surfaces from contamination and in particular to systems and methods for sterilizing such equipment using ultraviolet (UV) radiation.

BACKGROUND OF THE INVENTION

Among the many burdens of daily living is a never-ending quest to fight germs and disease wherever they might be. Examples of that struggle are manifested in numerous products, such as disinfectant wipes, sprays, soaps and other products. The use of these types of sanitizing products is very widespread. From traditional bathroom environment uses, such as toilet seat covers, they have migrated to products suited for gymnasiums, classrooms, shopping malls and even supermarket shopping carts. Basically, wherever there is activity that involves any form of touching, there is oftentimes some cleaning product nearby which is designed to prevent the spread of germs and disease. This need for germ control is further pronounced in the modern world as a consequence of the increased threat of mass bio-terrorism, which often relies on quick-acting germ spreading mechanisms in order to propagate harmful agents.

Presently, there is a glaring gap in the sphere of germ-protective "coverage", namely, computer keyboards and other computer peripheral devices and add-ons. By design, the keyboard, mouse and similar interactive computer peripheral devices are meant to be touched as the primary means of communication between the user and a computer. Furthermore, these devices are often shared by many users, especially in public or office environments. In addition, since the keyboard (and mouse) is used at all times to work on the computer, even a single user of an unshared keyboard (and mouse) is highly exposed to contamination as the keyboard serves as an "accumulator" where bacteria, viruses and/or other germs or disease-causing agents become deposited over time and use.

Numerous studies have been performed that confirm the fact that keyboards are one of the leading mechanisms for spreading diseases, which may eventually lead to food poisoning and other illnesses. In these studies, keyboards were found, on average, to be five times more dirtier than toilet seats. Unfortunately, there is virtually nothing on the market that prevents this universally used computer peripheral component to be protected from one use to the next. It is this deficiency in preventing the spread of germs on keyboards and other computer peripheral devices that the present invention seeks to efficiently and effectively address.

Some products on the market today attempt to provide a solution to this universal problem. However, they do so in a very primitive way, that is, by largely covering the keyboard with a disposable plastic overlay. This approach is quite limited in utility in that it suppresses and in some instances eliminates the required need for tactile feel for the keyboard keys, and it also prevents the user from using touch-sensitive devices, such as touch-pads, trackballs, and the like, that are often built-in into modern keyboard devices. By placing anything on top of the keyboard the entire functionality of the keyboard surface is altered and full use is compromised to some extent. Moreover, the disposable overlay approach requires constant replenishment, i.e., on-going costs, which translates into endless purchasing of product as well as personnel to replace it. And, finally, disposable overlays do very little to promote a clean environment as they contribute to overall trash accumulation, and are often not readily biodegradable. In addition, none of the existing disposable overlay solutions address any add-on computer peripheral devices, such as the mouse, mouse pad, fingerprint scanner, flash memory, and so on, which also must be cleaned as they are also potential sources of germs and disease. In addition to the above deficiencies, it is virtually impossible to control the proper use as well as frequency of use of these overlays, which makes it extremely difficult to have any confidence in their effectiveness.

Examples of keyboard overlays may be found in U.S. Pat. Nos. 3,454,075; 4,922,980 and 5,944,432.

Ultraviolet radiation and ozone gas generation have also been proposed as alternative solutions to the problem of computer peripheral device contamination. For example, U.S. Pat. Nos. 6,278,122; 6,458,331; 6,720,950 and 7,372,044 and Published U.S. Patent Application Nos. 2008/0067417; 2009/0123331 and 2009/0218512 disclose the use of UV and/or ozone generation chambers which are adapted to enclose computer keyboards, mice and similar computer peripheral devices during a sanitation procedure. While they may be effective for their intended purposes, the very existence of bulky chambers at the computer workstation area, which may be quite limited in available space, renders these devices less than desirable as a practical matter.

Published U.S. Patent Application No. 2004/0028553 teaches the use of pulse radiation as a means of sterilizing objects such as pieces of mail and keyboards. However, the system employed in that patent application requires the use of two cooperating conveyors over which the objects to be sanitized are conveyed. Obviously, such a system would be very impractical, and expensive, if installed at a typical computer workstation area.

Finally, although not described as being useful for disinfecting computer peripheral devices, U.S. Pat. Nos. 5,920,075 and 6,953,940, as well as Published U.S. Patent Application No. 2008/0260601, disclose the use of hand-held UV-generating wands for sanitizing objects and room surfaces. A fundamental disadvantage of such hand-held devices is that they require human beings to hold and move the wands steadily over desired surfaces for predetermined periods of time in order to achieve sterilization. As will be appreciated, any human involvement in the wand-handling procedure reduces the likelihood of effective disinfection, especially if the wand is being handled by inexperienced, unskilled, or impatient personnel. Moreover, the wand itself acts as a medium for the accumulation and dissemination of germs, particularly if the same wand is used by multiple people such as might occur in connection with public use computers, for example.

Furthermore, none of the aforementioned systems and methods provide a reliable way of monitoring and/or guaranteeing that the sterilization process has occurred, that it has been preformed correctly, or when and how it was done.

An advantage exists, therefore, for an enclosureless system which utilizes UV radiation as the disinfecting medium for sterilizing computer peripheral devices, but which preferably avoids handling of the sterilization device by a human being.

A further advantage exists for a UV radiation disinfection system which monitors the computer peripheral device sterilization process and guarantees that the process has occurred correctly prior to use of a host computer.

SUMMARY OF THE INVENTION

The system according to the invention allows virtually complete sterilization of the surface of a computer keyboard (or other computer peripheral devices) without creating any ill effects to the peripheral device or its surface. The system simultaneously eliminates on-going material and labor costs while assuring proper usage of the sterilizing system, including guaranteeing that a sterilization procedure has been performed.

The system utilizes a wand-type UV light source movably mounted above a computer keyboard or other computer peripheral device to be sanitized. The UV light source is preferably moved across the keyboard surface the surfaces of any add-on peripheral devices to eliminate nearly all germs, bacteria, viruses, pathogens and other microorganisms that have accumulated on the surfaces of the keyboard and other peripherals. Desirably, the system operation is managed by a controller device, which may be plugged into a host computer via USB or other suitable connection. The controller device monitors the operation, rate and movement of the light source to assure compliance, as well as prevent use of the peripherals being sanitized unless the disinfection process has been performed properly.

The invention provides an extremely effective, compact, controlled and virtually cost-free and environmentally-friendly solution to disinfecting keyboard and other peripheral device surfaces.

There are many advantages to the invention. Among others, it allows the user complete flexibility as to the frequency and thoroughness of the process. Furthermore, since there are no replaceable or disposable parts in the process (other than occasional replacement of the UV generating lamp), the disinfection process can be repeated as much or as little as desired by the user. That is to say, a home office user may need to use the device less frequently than a public office user. In addition, the controller device may be programmed to impose universal operational rules, so that at least a minimum usage level is performed and maintained, thereby allowing for total confidence and control of the effectiveness of the process.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings wherein.

DETAILED DESCRIPTION OF THE INVENTION

Figure 1:
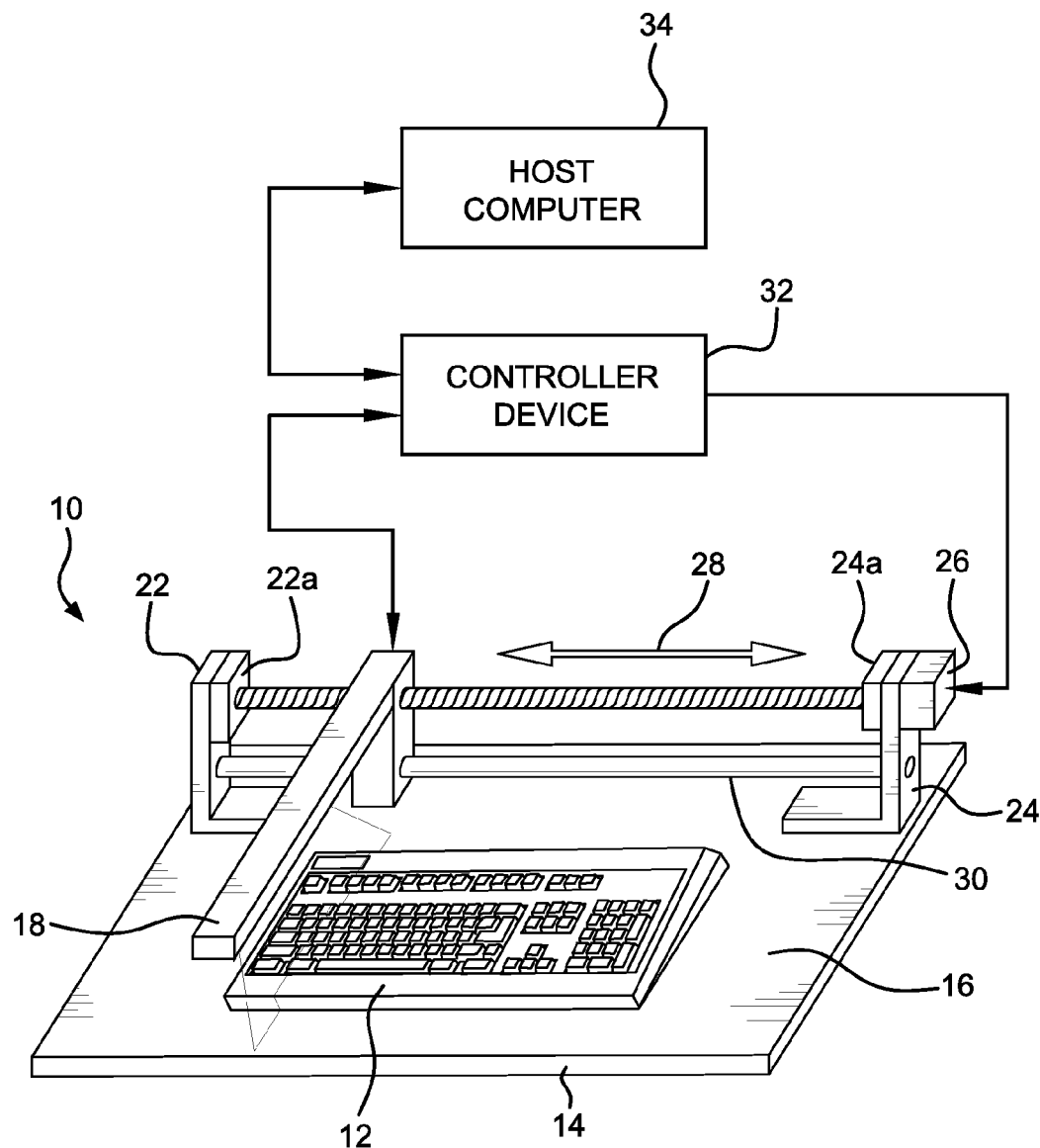
FIG. 1. is a perspective view of a first embodiment of a computer peripherals sterilization system according to the present invention.

Referring to the drawings wherein like or similar references indicate like or similar elements throughout the several views, there is shown in FIG. 1 a computer peripherals sterilization system according to the present invention which is identified generally by reference numeral 10.

A keyboard (or other peripheral device) 12 to be sterilized is placed on top of a base means 14. The base means supports the peripheral device(s) and defines the overall active disinfection area of the invention, which disinfection area may include an expansion area 16 for supporting unillustrated peripherals such as a mouse, a mouse pad, and other add-on peripherals that are subject to contamination.

A UV light assembly 18, preferably in the form of a wand-type UV lamp, is connected to and movably situated above base means 14. System 10 further includes means for moving the UV light assembly across the base means whereby ultraviolet radiation emitted by the UV light assembly is directed toward the base means and sterilizes computer peripheral devices, such as keyboard 12, supported by the base means. By way of example but not limitation, the means for moving the UV light assembly may comprise a screw jack threadedly engaged with UV light assembly 18. Opposite ends of screw jack 20 are rotatably received in end stops 22 and 24 which are attached by suitable means to base means 14. The end stops define respective Starting and Ending Nodes, discussed below, and are preferably equipped with limit sensors 22a and 24a to stop turning of screw jack 20 when the UV light assembly approaches the end stops. A reversible motor 26 is connected to one of the end stops, e.g., end stop 24, and rotates screw jack 20 in opposite directions to translate UV light assembly 18 across the surface of the computer peripheral device(s) to be treated in the directions indicated by double-headed arrow 28. In order to prevent unwanted rotation of UV light assembly about the threaded screw jack 20, it is preferred that system 10 include guide means 30. In the illustrated example, guide means 30 is a rod that is affixed at its opposite ends to end stops 22 and 24. The rod also passes through the UV light assembly 18 whereby the UV light assembly slides over the rod. It will be understood, however, that guide means 30 may comprise other means such as grooves or similar structure provided in the upper surface of base means 14 that permit translational movement of the UV lamp assembly 18 yet prevent rotational movement thereof. It will be further understood that the means for moving UV light assembly across the base means may comprise other means for imparting linear motion such as a pneumatic or hydraulic cylinder or the like, although such cylinders may add size and complexity to the overall system.

The operation of system 10 is generally as follows. The operation is preferably substantially to completely controlled by a controller device 32 and/or a host computer (discussed below). Beginning at sensor 22a located at the Starting Node, i.e., end stop 22, the UV lamp assembly 18 is first automatically or manually turned on to thereby emit UV radiation toward the base means 14. Then, motor 26 (or a similar driver) is activated and the lamp assembly is driven across the upper surface of keyboard 12 by the moving means 20 in such fashion that the UV radiation emitted by the lamp assembly neutralizes or kills any surface-based bacteria viruses, fungi, molds, and other undesirable pathogens and microorganisms on keyboard 12. That is, moving means 20 will desirably move at an suitable speed and the radiation from the UV light assembly 18 will be of suitable intensity so as to disinfect the surface of the keyboard. Following disinfection of the keyboard, the UV light assembly 18 may then be moved until it is above the expansion area 16, which can support a mouse, a mouse pad, USB stick(s) or any other presently known or hereinafter developed add-on peripheral devices that the user wishes to disinfect. Upon reaching the process end point, i.e., limit sensor 24a of end stop or Ending Node 24, the UV lamp assembly 18 is then manually or, more preferably, automatically turned off. The moving means may then be instructed by the controller device 32 to return the UV light assembly 18 to Starting Node 22 by reverse operation of motor 26. Alternatively, UV light assembly 18 may be automatically returned to the Starting Node upon restart of the system. Still further, the UV light assembly may be manually returned by a user, although such action requires touching, and possible contamination, of the UV light assembly.

Figure 2:
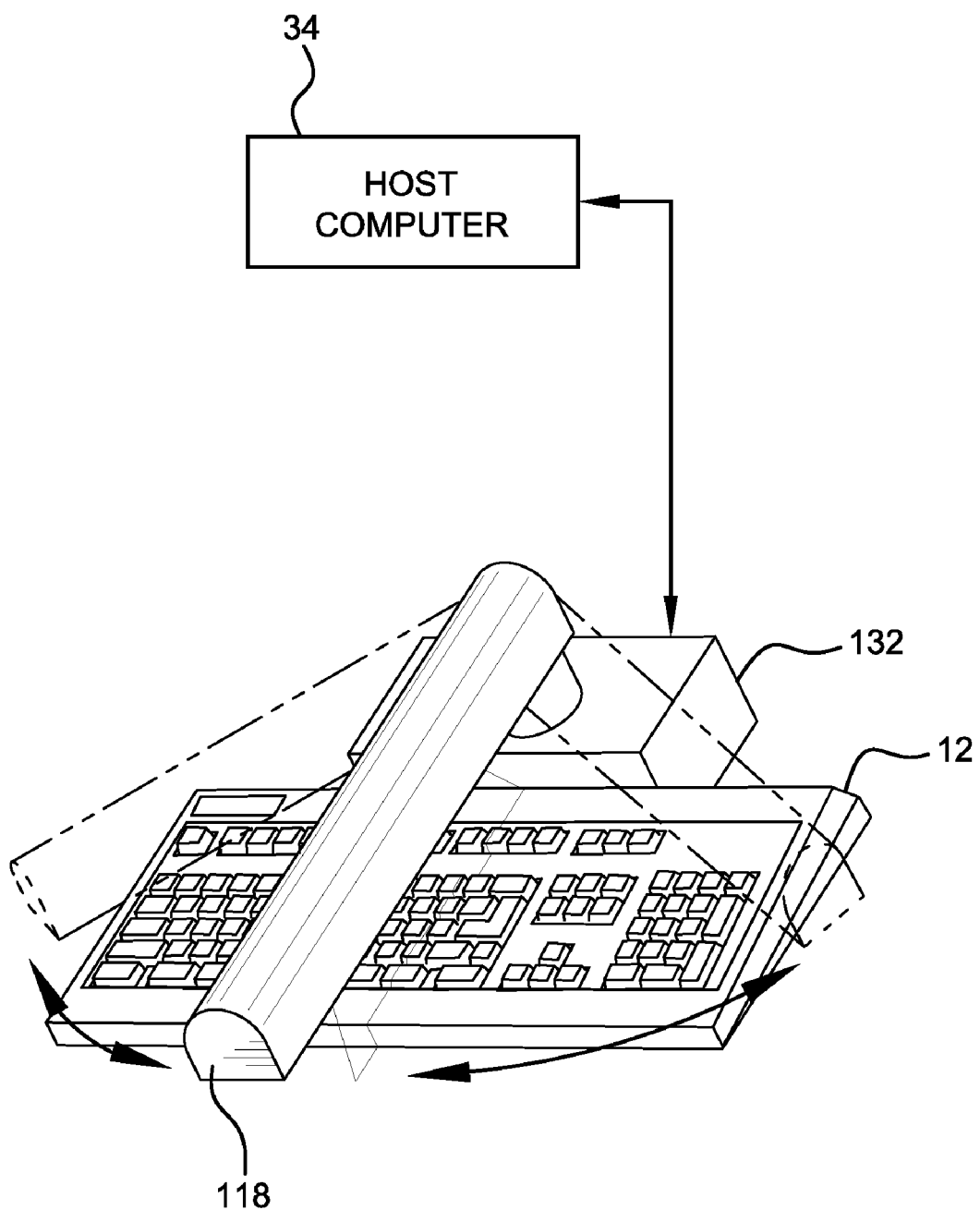
FIG. 2. is a perspective view of a further embodiment of a computer peripherals sterilization system according to the present invention.

FIG. 2 depicts an alternative embodiment of the system according to the present invention which is identified generally by reference numeral 110. In system 110, rather than translational motion, a wand-like UV lamp assembly 118 moves across the surface of a keyboard 12 or other peripheral device to be sanitized in a semi-circular rotational motion akin to that of an automobile windshield wiper. That is, a UV lamp assembly 118 is pivotally or rotationally mounted to a controller device 132, discussed below, which causes the lamp assembly to sweep across the surface of the keyboard in a semi-circular rotational path. The arcuate path of the UV lamp assembly 118 may begin at a generally central location with respect to the keyboard 12 as shown in FIG. 2, or it may begin at a first end of the keyboard. In either case, the UV lamp assembly 118 preferably travels through an angle of arc of up to about 180° in order to enable UV radiation to cover the entire surface area of the keyboard 12 or other peripheral devices or objects to be sanitized.

Controller device 132 preferably includes an unillustrated reversible motor similar to motor 26 of system as well as unillustrated limit sensors that limit the range of motion of UV lamp assembly 118. Alternatively, the UV light assembly 118 of FIG. 2 may be manually pivoted by a user, although such action requires touching, and possible contamination, of the UV light assembly.

The following discussion refers to both the controller device 32 of FIG. 1 and the controller device 132 of FIG. 2. The controller device 32 or 132 desirably manages when the system is to be activated and how it is to be used. The controller device 32 or 132 may be plugged into a host computer 34 via a USB connector or other suitable presently known or hereinafter developed connection means. Controller device 32 or 132 may receive its commands from either or both an internal processor or the host computer 34. The host computer may be programmed to enable operation of system 10 or 110 at any time such as during boot-up or some other time. Once a request or command to perform a disinfection process (or sterilization transaction) is issued, instructive prompts may appear on the monitor of host computer 34. Such prompts may include, for example, prompts to turn on the UV lamp assembly 18 or 118 and to move the UV light assembly (although such actions may be programmed within controller device 32 or 132 to occur automatically).

Controller device 32 of FIG. 1 preferably measures the time it takes the UV lamp assembly 18 to move from the Starting Node at end stop 22 to the Ending Node at end stop 24. Similarly, controller device 132 of FIG. 2 preferably measures the time it takes the UV lamp assembly 118 to move through an angle of arc sufficient to cover keyboard 12 and/or other peripheral devices. In either case, if this time does not comport with the required rate of movement, controller device 32 or 132 may require the process to be repeated or require the user return the UV lamp assembly back to a starting position. Preferably, only upon successful interactions between the user and system 10 or 110 will the user be allowed to continue to use the keyboard in a normal fashion—at least until the next request to initiate a sterilization operation is issued by the host computer or the controller device. Successful interactions between the user and system 10 or 110 are determined by rules stored in the controller device and/or host computer which govern such wand parameters as velocity, angle or distance traversed, end points and system power. The rules thus determine not only whether a sterilization procedure has been performed but also whether it has been performed correctly.

For example, if the UV lamp assembly 18 or 118 either fails to cover its prescribed range of motion or covers such range too quickly, the controller device or the host computer may require the process to be repeated. Relatedly, if the system is configured such that the UV lamp assembly 18 or 118 is to be operated manually, then the controller device 32 or 132 or the host computer 34 may be programmed with rules that will prevent the host computer from functioning unless a user properly performs a sterilization transaction within a predetermined number of attempts. For instance, in public use environments such as schools and libraries, if a user fails to successfully perform a disinfection transaction within, say, three tries, then the host computer will be deactivated and the user will be automatically alerted to seek assistance from library staff or other attendant.

It will be appreciated that other possible variations in operation and control flow are readily attainable. For example, a rule may be set up on controller device 32 or 132 or host computer 34 whereby every time the computer is turned on, the user must perform at least one sterilization transaction in order to continue using the computer. This is extremely beneficial for public use machines, such as those at libraries, schools or universities where there are typically many different users throughout the course of a day. This unique capability allows the computer owner to create and maintain minimum levels of cleanliness, even in their own home. In addition, since the use of the system is "known" by the host computer 34, the process can be easily animated on the computer's monitor screen, and made user friendly by employing graphics, various languages, prompts, and so on. Additionally, the system is capable of monitoring its own usage to make sure that the disinfection process is performed in a defined fashion. Usage statistics can easily be generated via reports and accumulated data. Furthermore, the process can also be prompted by various rules that may be set up to periodically interrupt the user and require him or her to perform a sanitation transaction or operation. Still other possibilities of automating the process and recording its performance will be apparent to one of ordinary skill in the art.

A further advantage of the present invention is that it allows users to gather information regarding the frequency and success of sterilization transactions performed on computer peripheral devices. Such data may be collected either on the host computer 34 or the controller device 32 or 132. A user can then conduct any variety of detailed statistical analyses of such gathered information as he or she may desire.

It will be further understood that while the invention herein described has been thus far primarily directed to a UV lamp assembly which is moved by electromechanical means, it is also conceivable that UV light assembly 18 or 118 may be moved purely by human force. That is, the motor 26 of FIG. 1 or the internal motor of controller device 132 of FIG. 2 may be eliminated. In that event, in the system 10 shown in FIG. 1, UV light assembly may 18 be manually slid back and forth along a pair of guide rods or other guide structure, whereas in the system 110 shown in FIG. 2, UV light assembly may 118 may be manually swung or pivoted through a suitable range of arc, e.g., up to about 180°. While possible, such scenarios are not preferred as they introduce human control into the sanitizing operation and would tend to soil the UV light assembly.

Although the invention has been described in detail for the purpose of illustration, it is to be understood that such detail is solely for that purpose and that variations can be made therein by those skilled in the art without departing from the spirit and scope of the invention as claimed herein.

What is claimed is:

1. A method for sterilizing at least one computer peripheral device comprising the steps of:
   providing an ultraviolet light assembly and means for enabling movement of said ultraviolet light assembly across at least one computer peripheral device;
   emitting ultraviolet radiation from said ultraviolet light assembly toward at least one computer peripheral device;
   performing a sterilization transaction on at least one computer peripheral device by controlling said ultraviolet light assembly and said means for enabling movement; and
   determining the time it takes said ultraviolet light assembly to move from a starting point to an ending point to complete a sterilization transaction and, if such time does not comport with a required rate of movement, repeating the sterilization transaction.

2. The method of claim 1 further comprising providing a controller device in operative communication with said ultraviolet light assembly and said means for enabling movement of said ultraviolet light assembly.

3. The method of claim 2 wherein said controller device is in further communication with a host computer.

4. The method of claim 3 wherein, when a host computer is activated, said controller device or the host computer prompts a user to perform a sterilization transaction.

5. The method of claim 1 further comprising generating an alert if a sterilization transaction is not performed or is not performed properly.

6. The method of claim 1 wherein the method is performed in an enclosureless environment.

7. A method for sterilizing at least one computer peripheral device comprising the steps of:
   providing an ultraviolet light assembly and means for enabling movement of said ultraviolet light assembly across at least one computer peripheral device;
   emitting ultraviolet radiation from said ultraviolet light assembly toward at least one computer peripheral device;
   performing a sterilization transaction on at least one computer peripheral device by controlling said ultraviolet light assembly and said means for enabling movement; and
   periodically prompting a user to perform a sterilization transaction.

8. A method for sterilizing at least one computer peripheral device comprising the steps of:
   providing an ultraviolet light assembly and means for enabling movement of said ultraviolet light assembly across at least one computer peripheral device;
   emitting ultraviolet radiation from said ultraviolet light assembly toward at least one computer peripheral device; and
   performing a sterilization transaction on at least one computer peripheral device by controlling said ultraviolet light assembly and said means for enabling movement wherein, if said ultraviolet light assembly fails to move through a prescribed range of motion or covers such range too quickly, then repeating the sterilization transaction.

9. A method for sterilizing at least one computer peripheral device comprising the steps of:
   providing an ultraviolet light assembly and means for enabling movement of said ultraviolet light assembly across at least one computer peripheral device;
   emitting ultraviolet radiation from said ultraviolet light assembly toward at least one computer peripheral device; and
   performing a sterilization transaction on at least one computer peripheral device by controlling said ultraviolet light assembly and said means for enabling movement wherein, if a user fails to properly perform a sterilization transaction within a predetermined number of attempts, then deactivating a host computer of said at least one computer peripheral device.

10. A method for sterilizing at least one computer peripheral device comprising the steps of:
    providing an ultraviolet light assembly and means for enabling movement of said ultraviolet light assembly across at least one computer peripheral device;
    emitting ultraviolet radiation from said ultraviolet light assembly toward at least one computer peripheral device;
    performing a sterilization transaction on at least one computer peripheral device by controlling said ultraviolet light assembly and said means for enabling movement;
    performing a sterilization transaction every time a host computer of said at least one computer peripheral device is activated; and
    preventing operation of a host computer of said at least one computer peripheral device if a sterilization transaction is not performed properly upon activation of the host computer.

11. A method for sterilizing at least one computer peripheral device comprising the steps of:
    providing an ultraviolet light assembly and means for enabling movement of said ultraviolet light assembly across at least one computer peripheral device;
    emitting ultraviolet radiation from said ultraviolet light assembly toward at least one computer peripheral device;
    performing a sterilization transaction on at least one computer peripheral device by controlling said ultraviolet light assembly and said means for enabling movement; and
    preventing operation of a host computer of said at least one computer peripheral device if a sterilization transaction is not performed upon activation of the host computer.

12. A method for sterilizing at least one computer peripheral device comprising the steps of:
    providing an ultraviolet light assembly and means for enabling movement of said ultraviolet light assembly across at least one computer peripheral device;
    emitting ultraviolet radiation from said ultraviolet light assembly toward at least one computer peripheral device;
    performing a sterilization transaction on at least one computer peripheral device by controlling said ultraviolet light assembly and said means for enabling movement; and
    gathering statistical information regarding at least one of the frequency and success of sterilization transactions performed on computer peripheral devices.

13. The method of claim 12 further comprising performing statistical analyses on the gathered statistical information.

* * * * *